United States Patent
Mays

[11] Patent Number: 5,236,361
[45] Date of Patent: Aug. 17, 1993

[54] DENTAL POST

[76] Inventor: Ralph C. Mays, 10322 B E. 58th St., Tulsa, Okla. 74146

[21] Appl. No.: 892,755

[22] Filed: Jun. 3, 1992

Related U.S. Application Data

[63] Continuation-in-part of Ser. No. 675,735, Mar. 27, 1991, abandoned.

[51] Int. Cl.⁵ .................................................. A61C 5/08
[52] U.S. Cl. ........................................ 433/221; 433/220
[58] Field of Search ........................ 433/220, 221, 173

[56] References Cited

U.S. PATENT DOCUMENTS

| | | | |
|---|---|---|---|
| D. 273,984 | 5/1984 | Vlock | 433/225 |
| 1,018,803 | 2/1912 | Anderberg | |
| 1,524,409 | 1/1925 | Simmons | |
| 2,705,837 | 4/1955 | Gerlach | |
| 3,434,209 | 3/1969 | Weissman | |
| 4,180,910 | 1/1980 | Straumann et al. | 433/173 |
| 4,253,835 | 3/1981 | Ware | 433/220 |
| 4,355,978 | 10/1982 | Ericson | 433/220 |
| 4,479,783 | 10/1984 | Weissman | 433/221 |
| 4,490,116 | 12/1984 | Deutsch et al. | 433/215 |
| 4,600,391 | 7/1986 | Jacob | 433/220 |
| 4,600,392 | 7/1986 | Weissman | 433/225 |
| 4,684,555 | 8/1987 | Neumeyer | 428/36 |
| 4,708,655 | 11/1987 | Weissman | 433/225 |
| 4,818,559 | 4/1989 | Hama et al. | 427/2 |
| 4,820,159 | 4/1989 | Weissman | 433/225 |
| 4,952,150 | 8/1990 | Schiwiora et al. | 433/220 |
| 5,074,792 | 12/1991 | Bernadat | 433/220 |

Primary Examiner—Gene Mancene
Assistant Examiner—Cindy A. Cherichetti
Attorney, Agent, or Firm—Head & Johnson

[57] ABSTRACT

An improved dental post formed of a unitary, elongated metal post having a proximal portion and a distal portion, the distal portion being configured to be received in a prepared drill hole in a tooth, the proximal portion being configured to extend externally of a tooth to receive a dental device, such as a crown, thereon, the proximal portion having a porous surface to which dental device materials securely adhere, the porous surface preferably having interconnected interstices. In one embodiment the post distal portion is irregularly configured to thereby accept a crown having a highly contoured configuration.

12 Claims, 2 Drawing Sheets

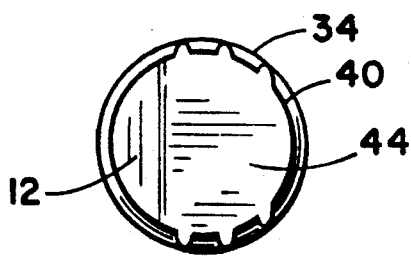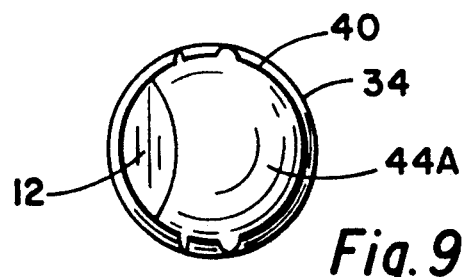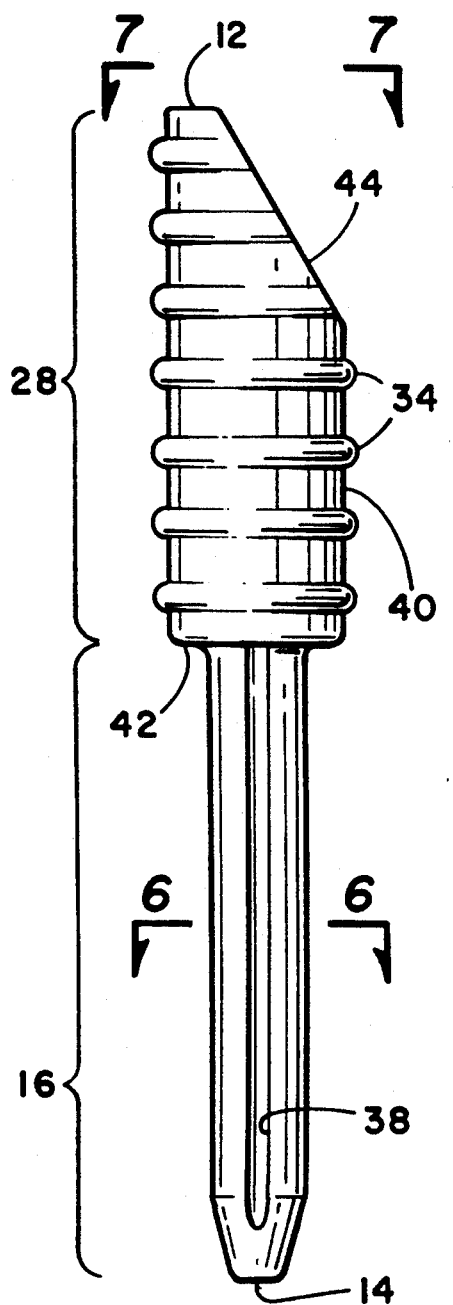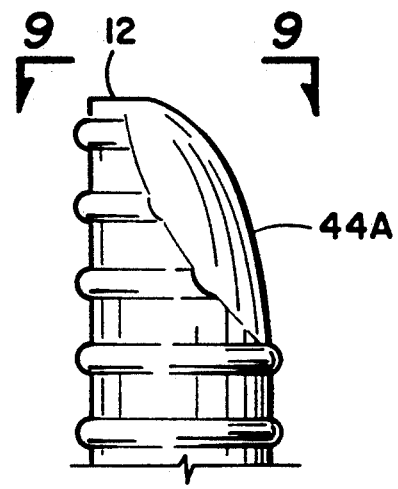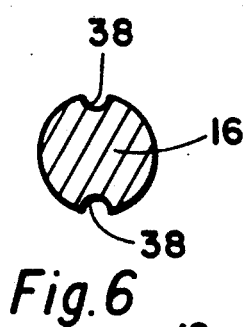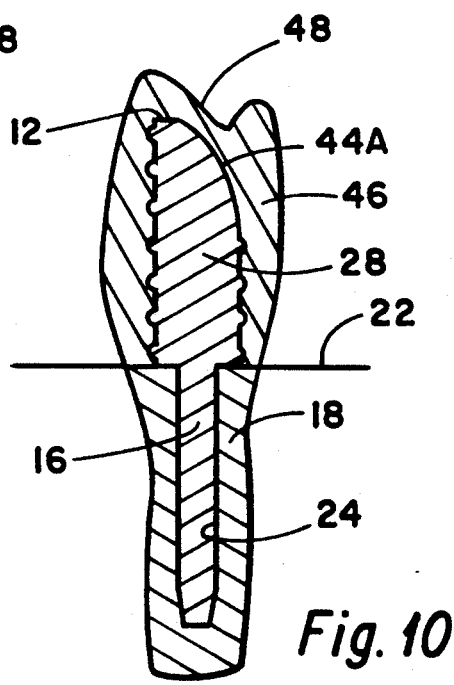

DENTAL POST

CROSS-REFERENCE

This is a continuation-in-part application of pending U.S. application No. 07/675,735, filed 27 Mar. 1991, now abandoned entitled "Improved Dental Post."

BACKGROUND OF THE INVENTION

This invention relates to an improved device for mounting in a drill hole formed in a natural tooth to provide means for more securely supporting a dental device, such as a crown, to the tooth or for use in filling a tooth.

Frequently, human teeth are worn or broken away to the point where an insignificant amount of the tooth extends above the gum line to support a crown or wherein the portion that does extend above the gum line is of rounded or other configuration that does not lend itself to securely receiving a crown. To more securely support a dental device, such as a crown, onto a tooth others have suggested extending pins or posts into the tooth so that a portion of the pin or post extends externally of the tooth and serves as a reinforcing member for receiving an appliance. For reference to prior devices mounting in teeth, reference can be had to the following previously issued United States Patents: U.S. Pat. Nos. 4,490,116; 4,479,783; 3,434,209; 2,705,837; 1,018,803; 1,524,409; 1,524,409; Des 273,984; 4,820,159; 4,778,389; 4,708,655; and 4,600,392.

The present disclosure is an improved dental post having advantages over other dental posts known at the present time, including those illustrated and described in the above mentioned U.S. patents.

SUMMARY OF THE INVENTION

The present disclosure is an improved dental post in the form of a unitary, elongated metal member having a proximal portion and a distal portion. The post distal portion is configured to be received in a prepared drill hole in a tooth. The configuration of the distal portion may take several forms, but a preferred arrangement includes the provision of shallow-depth external threads on the outer surface of the dental post. These threads serve to securely engage the wall of a borehole drilled in a tooth.

In the typical manner of mounting a dental post in a tooth, the dentist bores a hole of selected diameter more or less following the tooth's root canal. The borehole is drilled from the tooth external surface into the tooth but is drilled less than the total depth of the tooth so that no portion of the borehole extends externally of the tooth, except for the outer end of the tooth where the borehole enters the tooth.

The post is arranged so that the proximal portion thereof extends externally of the tooth to receive a dental device, such as a crown or filling. The proximal portion may be externally shaped in a variety of configurations, preferably with a noncylindrical surface so as to increase the mechanical interrelationship between the post proximal end external surface and the dental appliance which is secured to such surface.

The external surface of the proximal portion has a porous surface to which dental device material securely adheres. This porous surface is preferably more than a mere mat finish, but includes interstices, that is, wherein the surface is defined at least in part by small irregular internal passageways. In the most preferred arrangement at least some of the interstices passageways extend from the external surface and interconnect with outer passageways that also extend from the external surface.

The improved dental post of this disclosure may be manufactured such as by machining a post of a generally desired external configuration and subjecting the formed structure, or at least the proximal end portion, to a bath of solvent of the type that dissolves away a portion of the post surface. When the post is formed of stainless steel, titanium or the like, a solvent, such as hydrochloric or dilute sulfuric acid, is used to dissolve portions of the surface around grain boundaries in the metal to form dendrites. The dendritically configured surface of the metal post provides superior bonding characteristics compared to an untreated titanium post.

In a more preferred method of practicing the invention, the dental post structure is formed of a mixture of stainless steel or titanium and another more soluble metal so that when the post is subjected to a solvent the soluble metal is preferentially dissolved, leaving the stainless steel or other host metal substantially unaffected. In this arrangement stainless steel, titanium or other host metal and another more soluble metal are intermixed in such a way that the solvent attacking the other metal or more soluble material at the post surface forms interstices within the surface area.

As an example of practicing the invention, stainless steel or titanium is mixed with aluminum in a non-homogenous mixture. The post is formed of such mixture and is then subjected to a solvent, such as hydrochloric acid or sulfuric acid that primarily attack the aluminum to dissolve the same while leaving the titanium substantially unaffected.

The ideal dental post that is used as a foundation for a dental device, such as a crown formed on the top of a tooth where the upper portion has been removed and the dental post anchored in the remaining root portion of the tooth, should, for most effective results, be as strong as possible. This requires the dental post to be of significant diameter and size to securely support a crown formed thereon. In forming a crown the practitioner must accommodate the patience's other teeth. First, a crown must be formed so as to have the size, shape and contours of a natural tooth. Second, the crown must match the adjacent teeth and the tooth that it impacts against during chewing action. For these reasons, it is sometimes necessary to contour a crown in a regular fashion and when a post is of substantial diameter so as to provide the necessary strength and support, the external surfaces of the post may interfere with the desired ultimate configuration of the crown. To overcome this difficultly an improved embodiment of the invention provides a post that is contoured at one portion at the top and side so that the practitioner can orient the post when it is anchored in a tooth to accommodate the most desirable configuration of the crown, or other similar appliance, that is anchored onto the post.

A better understanding of the invention will be had by references to the following description and claims, taken in conjunction with the attached drawings.

DESCRIPTION OF THE DRAWINGS

FIG. 5 is an external elevational view of a dental post of an alternate embodiment that is specifically configured to provide increased adaptability for the support of a crown or other dental appliance having unique configurations.

FIG. 6 is a cross-sectional view of the post distal portion taken along the line 6—6 of FIG. 5 showing the employment of hydraulic and pneumatic pressure equalizing channels.

FIG. 7 is a top view of the embodiment of FIG. 5 taken along the line 7—7 of FIG. 5 showing the employment of a slanted surface partially defining the external surface configuration of the post proximal portion.

FIG. 8 is a fragmentary elevational view of the upper portion of the post proximal portion showing an alternate arrangement wherein the slanted surface is rounded.

FIG. 9 is a top view of the embodiment of FIG. 8 as taken along the line 9—9 of FIG. 8.

FIG. 10 is a reduced scale cross-sectional view of a post having the configuration of FIG. 8 with the distal portion inserted into a drill hole in a tooth and the proximal portion supporting a crown.

DESCRIPTION OF THE PREFERRED EMBODIMENT

Figure 1:
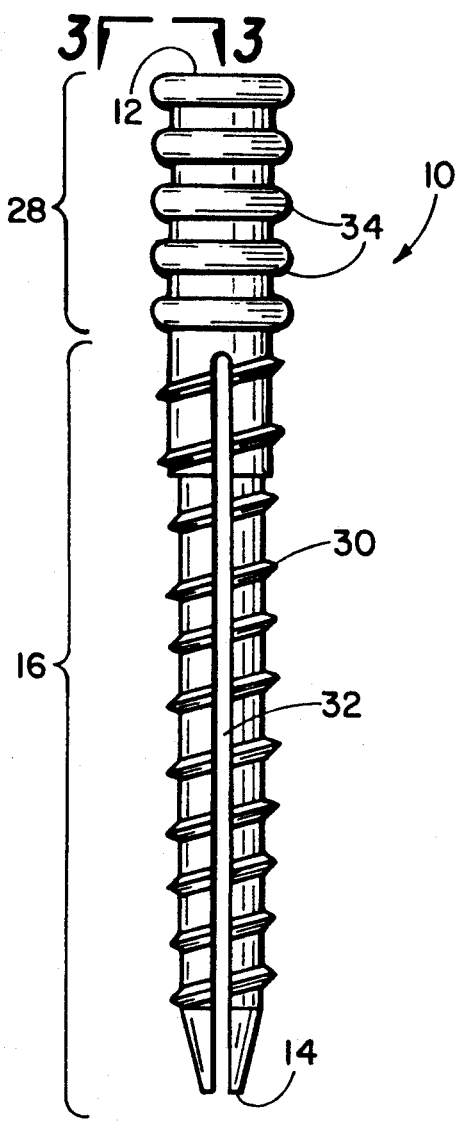
FIG. 1 is an external, elevational view of a dental post which incorporates the principles of this invention, the post being shown substantially larger than that utilized in actual practice.

Referring to the drawings and first to FIG. 1, a dental post which embodies the principles of this invention is generally indicated by the numeral 10. This disclosure is not concerned to a great degree with the specific external configuration of post 10, which is illustrated for exemplary purposes only, but this disclosure is primarily directed to the porous external surface of the post proximal end portion.

Figure 2:
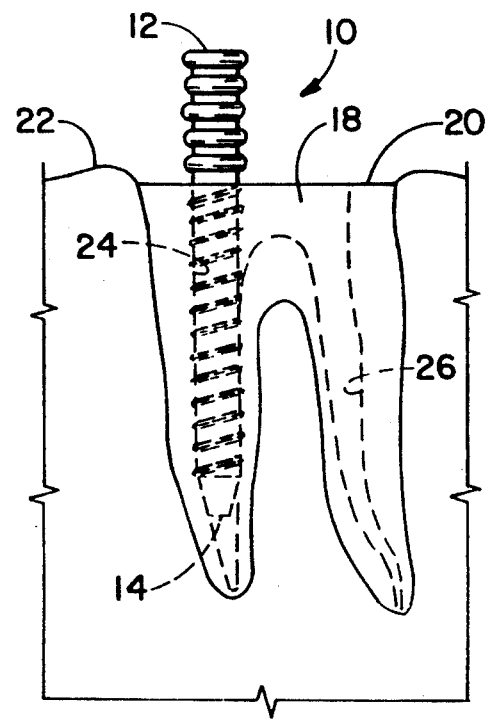
FIG. 2 is a diagrammatic view of a tooth structure shown in external, elevational view with the root canals therein formed in dotted outline, the tooth being positioned in the alveolar rigid of a patient and in which the tooth structure has the natural upper portion missing and showing a borehole having been formed in one portion of the tooth structure with a dental post of the type shown in FIG. 1 inserted therein.

Post 10 has a proximal end 12 and a distal end 14. Distal portion 16 of the post is configured to be received in a drill hole formed in a tooth. FIG. 2 shows post 10 mounted in a tooth 18. The tooth 18 has an upper surface 20 which is substantially coincident with the gum line 22. The tooth 18 in its natural occurring external configuration would have an upper portion extending substantially above the gum line which functions to provide biting and chewing surfaces. Due to accident, normal wear of teeth with age, chipping away of the tooth from normal wear and use, breaking away as a result of decay, or decay alone, and so forth, many individuals, particularly in older age or when subjected to traumatic accidents, have teeth of the type illustrated in FIG. 2 in which the lower portion, that is, the portion below gum line 22 is useable, but wherein the upper portion does not provide sufficient area to support a dental appliance, such as a crown. When an attempt is made to attach a crown to tooth 18 of FIG. 2, having an upper surface 20 that is not configured to lend itself to support a crown, failure of the dental appliance or crown frequently occurs. To improve the serviceability of a crown or other type of dental appliance, pin 10 is installed.

In order to install pin 10 a drill hole 24 is first formed by a dentist. The drill hole is of selected diameter that depends upon the nature of the tooth, that is, drill hole 24 must not be of sufficient diameter to extend externally of the tooth or to remove such a large part of the tooth that no structural support remains. The drill hole 24 typically follows the tooth root canal, such as root canal 26 shown in the right-hand portion of tooth 18.

Referring back to FIG. 1, dental post 10 has a proximal end portion 28. This is the portion which extends externally of the tooth when the post is installed, as shown in FIG. 2. The function of proximal portion 28 is to provide a structural member to which a dental appliance, such as a crown, can be secured to function as a replacement for the normal portion of the tooth extending above gum line 22, that is, to replace the function of the normal tooth which has been lost.

The post distal portion 16 is externally configured to be retained in drill hole 24 in a tooth. In the illustrated embodiment, distal portion 16 is provided with external threads 30 to aid in the insertion of the post in the tooth since the post may be threaded in the borehole to the desired depth. To provide retention force and to adjust for small differences in the interior diameter of drill hole 24 and the external diameter of post distal end portion 16, the distal portion is provided with an elongated slot 32 which allows the diameter of the distal portion to collapse slightly as the post is inserted into drill hole 24.

The post proximal portion 28 is configured to aid in the retention of a dental appliance, such as a crown, thereon. Therefore, the external shape of the proximal portion may vary. In the illustrated arrangement, the crown is formed with a series of short-length integral enlarged external diameter portions 34, the purpose of which is to resist the tendency of a crown or other appliance from being dislodged from the post. Chewing and biting action places a great stress on the teeth of an individual and therefore on a post implanted in a tooth. The pounds per square inch that can be created in biting is very high. In addition, in chewing action teeth are frequently moved laterally with respect to each other, causing side forces. Further, a crown must resist being pulled directly off of a tooth, such as occurs when the user chews sticky material, such as caramel candy and the like. For all these reasons, it is difficult to securely attach a crown to a tooth and to a post inserted in the tooth. Therefore, while the proximal end portion 28 may take a variety of configurations, a configuration other than a simple cylindrical surface is preferred.

Figure 3:
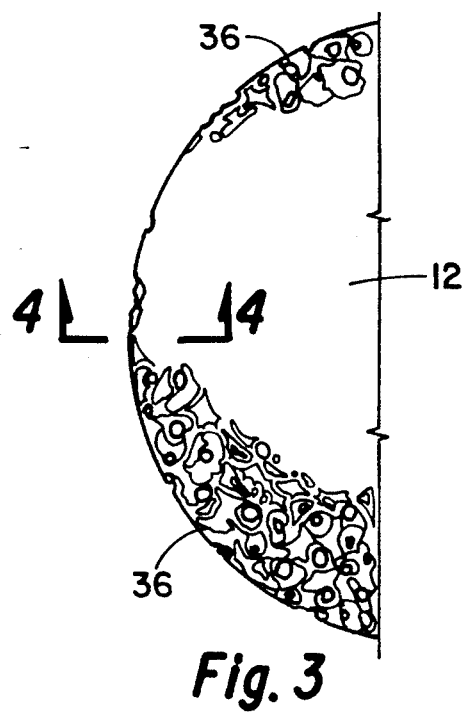
FIG. 3 is an enlarged partial plan view of the top of the dental post of FIG. 1, as taken along the line 3—3 of FIG. 1, showing the porous surface formed on the dental post proximal end portion.

Of significance to this disclosure is the texture of the external surface of the peripheral end portion. FIG. 3 is a highly enlarged partial top view of proximal portion 28 showing the surface thereof which is highly porous. The porosity is such that in the preferred embodiment the surface has interstices that connect with the external surface providing through passageways. The highly porous proximal end with interstices provides a surface into which material used in forming a crown, or used in adhering a crown to a post, can migrate. In other words, the surface of distal portion 28 is such that the adhesive or compost material forming a part of a dental appliance or crown does not merely engage the external surface of the proximal portion but actually, in part, penetrates into the surface to securely lock the dental appliance to the post proximal portion.

Figure 4:
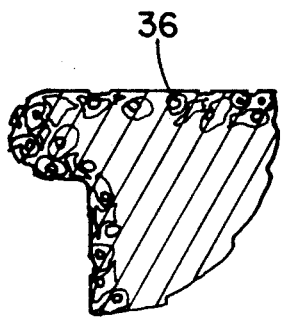
FIG. 4 is a fragmentary cross-sectional view taken along the line 4—4 of FIG. 3 showing a portion of the external surface of the dental post of FIGS. 1 and 3 in cross section, to show interstices formed in the external surface.

FIG. 4 is a small fragmentary cross-sectional view showing the highly porous surface of the post. The porosity of the post does not extend uniformly through the entire post or even through the post proximal portion, but extends only on the surface of the post proximal portion and then only to a depth of a fraction of a millimeter. The porosity having interstices therein is sufficient to improve bond with a dental application if the bonding material migrates into the external surface to a depth of at least about 0.1 millimeters.

The method of forming a dental post illustrated in FIGS. 1 through 4 will now be described as follows: A post structure is machined to have substantially the desired final configuration. The structure, and at least the portion thereof adjacent the external surface of proximal portion 28, is formed of stainless steel, titanium or similar metals or mixture of metals.

As an example, post 10 or at least the proximal portion 28 can be formed of stainless steel or titanium. When the post is formed of stainless steel or titanium a solvent, such as hydrochloric or dilute sulfuric acid, is used to dissolve portions of the surface around grain boundaries in the metal to form dendrites. The dendritically configured surface of the stainless steel or titanium post provides superior bonding characteristics compared to an untreated stainless steel or titanium post.

Another method of manufacturing the improved dental post is to use a mixture of stainless steel, titanium or other host metal mixed with aluminum. The mixture must be formed in a way so that the aluminum remains at least in part in particle configuration, that is, wherein the stainless steel, titanium or other host metal and aluminum are not homogeneously mixed. After the external configuration of the structure and particularly the proximal portion is formed, the proximal portion is subjected to the action of solvent of a type that preferentially dissolves the aluminum but not the host metal. For instance, where the post is formed of a mixture of stainless steel or titanium and aluminum, the use of a concentrated nitric acid can be employed to partially dissolve the aluminum without substantially attacking the stainless steel or titanium so that a highly porous surface if formed on the dental post.

It is apparent that other combinations of stainless steel or titanium and other more easily dissolved metals may be mixed to form the post basic structure that is then subjected to a solvent to dissolve away more soluble metal, leaving a highly porous surface.

Referring to FIGS. 5-10 an alternate embodiment of the invention is illustrated. FIG. 5 is an elevational view of a representative dental post that incorporates the principles of this invention and can be compared with FIG. 1. The post distal portion is indicated by 16 and the proximal portion by 28. The distal portion 16 is different than the embodiment of FIG. 5, that is, it does not have a split but is solid as illustrated in FIG. 6 and is of reduced diameter compared with the proximal portion 28. Further, the distal portion 16 of the embodiment of FIG. 5 does not include screw threads but is preferably cylindrical on the outer surface so that it can be inserted into a drill hole in a tooth without putting pressure on the tooth. The embodiment of FIG. 5 can be used wherein a drill hole is just slightly larger in internal diameter than the external diameter of the post distal portion 16. The post can then be inserted without pressure into the drill hole and retained in the drill hole by bonding material. In this way there is no force applied to the tooth root portion that would tend to cause the root portion to crack. Other types of posts that are designed for screw feed or other pressure fit anchoring into a drill hole in a tooth can, if not dimensioned very precisely, cause the tooth to crack. If the tooth does crack, it is substantially destroyed and would then have to be subsequently removed. The provision of a cylindrical distal portion as in FIGS. 5 and 6 substantially reduces the possibility of a tooth being cracked as it is inserted.

When positioning the distal portion in a drill hole in a tooth, the drill hole is first substantially filled with a bonding material. As the distal portion is inserted into the drill hole in a tooth some means must be provided for relieving any excessive bonding material. For this reasons, a groove or grooves 38 is or are provided in the distal portion 16 so that as the distal portion is gently inserted into the drill hole excessive liquid or gases can escape. Further, by the provision of one or more grooves 38 the dentist can be certain that sufficient bonding material has been placed in the drill hole since upon completion of the insertion of the distal portion sufficient bonding material should be displaced so that some bonding material is extruded out groove or grooves 38. If no such extrusion occurs, the dentist may realize that additional bonding material should be added.

While FIG. 6 shows the use of opposed grooves 38, in practice, only one groove is necessary. Therefore, the invention can be practiced with one or more grooves 38.

The post proximal portion 28 has a generally cylindrical external surface 40. Further, the external surface of the proximal portion 28 is defined by a top 12 and a bottom 42 that receives the integral distal portion 16. In this illustrated arrangement, the proximal portion cylindrical sidewall 40 is of a diameter greater than the diameter of the distal portion. Further, the proximal portion sidewall 40 is provided with integral enlarged diameter spaced apart ring portions 34, as previously described with reference to FIG. 1.

To successfully support a crown or other dental appliance onto the root portion of a tooth, it is important that the post be as strong as possible and preferably that the diameter, at least at the proximal portion, be fairly large. However, in providing a generally large diameter proximal portion, difficultly is sometimes encountered in the design of the configuration of the desired crown to be fitted on the post proximal portion. The crown must be configured to have the appearance of normal teeth. It must be of a size and shape to not only match adjacent teeth but to match the tooth against which the crown impinges during chewing action. For these reasons, a crown is usually of a specially designed contoured configuration. When the dental post proximal portion is as large in diameter as possible to thereby afford the maximum strength and support for the crown the dimensions of the post will sometimes interfere with the preferred configuration of the crown. For this reason, the improved dental post of FIG. 5 includes an angular surface 44. The angular surface 44 intercepts the post proximal portion top 12 and sidewall 40. The plane of the angular surface 44 preferably intercepts a plane of the cylindrical axis of sidewall 40 at an angle of about 20 to 60 degrees.

FIG. 8 shows the upper portion of the post as in FIG. 5 but wherein the angular surface 44A is rounded.

FIG. 10 is a reduced-dimension illustration of the employment of the improved dental post using the embodiment of FIG. 8. The root portion of a natural tooth 18 is provided with a drill hole 24 as previously described with reference to FIG. 2. The post distal portion 16 is inserted into and bonded in drill hole 24. The post proximal portion 28 extends above the gum line 22 and receives a dental appliance such as a crown 46 thereon. The crown 46 may be made of a variety of materials as employed in the dental profession and is typically provided with an external configuration 48 that simulates a natural tooth and which must conform in size and shape to fit adjacent teeth and must also conform in configuration to match teeth with which the crown impinges during chewing action. These requirements sometimes means that the post would interfere if it was of a totally cylindrical configuration. The provision of the angular surface 44A permits the practitioner to accommodate a larger variety of external configurations 48 for the crown than would otherwise be possible. The practitioner orients the angular surface 44A as required according to the configuration of the crown. It can be seen that the arrangement of FIG. 10 provides a post that provides maximum structural support for the crown 46 but in a way that does not require the practitioner to avoid using the most desired external configuration for the crown.

It is understood that the dental posts of FIGS. 5-10 are preferably provided with an external surface as described with reference to FIGS. 1-4, that is, a surface which has interstices formed therein for the intrusion of the material forming crown 46. The provision of the etched surface of this disclosure may be employed for both the proximal portion 28 and the distal portion 16, however, it is particularly important for the proximal portion 28.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An improved dental post comprising:
a unitary, elongated rigid metal post having a proximal portion and a distal portion, the distal portion being configured to be received in a prepared drill hole in a tooth and the proximal portion being configured to extend externally of a tooth to receive a dental device, such as a crown, thereon, wherein at least said proximal portion has an etched porous surface to which dental device materials securely adhere, the porous surface having interstices of dimension to receive the intrusion of crown forming materials therein.

2. A method of manufacturing an improved dental post comprising:
forming a dental post structure having a distal portion adopted to be inserted into and retained in a dentally prepared drill hole and having a proximal portion adapted to support a dental appliance thereon, the structure being formed of a mixture of a metal and another more soluble material; and
subjecting the formed structure to a bath of solvent of the type that preferentially dissolves the more soluble material to form a porous surface on the structure.

3. The method of manufacturing an improved dental post according to claim 2 wherein said more soluble material is aluminum.

4. The method of manufacturing an improved dental post according to claim 2 wherein the solvent is an acid solution.

5. A method of manufacturing an improved dental post comprising:
forming a dental post structure having a distal portion adapted to be inserted into and retained in a dentally prepared drill hole and having a proximal portion adapted to support a dental appliance thereon, the structure being formed of metal; and
subjecting the formed structure to a bath of solvent that dissolves portions of the surface around grain boundaries in the metal to form dendrites therein, the surface thereby becoming dendritically configured to have interstices therein.

6. A dental post comprising:
a unitary, elongated metal post having proximal portion and a distal portion, the distal portion being configured to be received in a prepared drill hole in a tooth, the proximal portion having an asymmetrical external surface defined by a generally cylindrical sidewall, a bottom that integrally connects to said distal portion, a top and an angular surface intercepting a portion of said top and a portion of said cylindrical sidewall and being spaced from another portion of said top that is semi-cylindrical and from another portion of said sidewall that is cylindrical adjacent said bottom whereby a dental appliance, such as a crown, may be formed onto and surround said post proximal portion, such appliance having a configuration that, without said angular surface, would expose a portion of said proximal portion top and cylindrical sidewall.

7. A dental post according to claim 6 wherein said angular surface is of rounded configuration.

8. A dental post according to claim 6 wherein at least said proximal portion external surface defined by said generally cylindrical sidewall, said top and said angular surface is porous so that dental device material will securely adhere thereto.

9. A dental post according to claim 8 wherein said at least proximal portion external surface that is porous has a porosity such as to have interconnecting interstices dimensioned to receive the intrusion of dental device forming materials therein.

10. A dental post according to claim 6 wherein said proximal portion generally cylindrical sidewall has integral enlarged external diameter spaced apart ring portions.

11. A dental post according to claim 6 wherein said distal portion has a substantially cylindrical surface coaxial with said proximal portion generally cylindrical sidewall, and wherein said distal portion is of reduced diameter compared to said proximal portion.

12. A dental post according to claim 11 wherein said distal portion has a groove in said substantially cylindrical surface providing means for relief of any fluids or gases as said distal portion is inserted in a prepared drill hole in a tooth.

* * * * *